US012699098B2

(12) United States Patent (10) Patent No.: US 12,699,098 B2
Lerner et al. (45) Date of Patent: Aug. 4, 2026

(54) FLOW VIROMETER FOR RAPID DETECTION OF INTACT VIRUSES

(71) Applicants: YISSUM RESEARCH DEVELOPMENT COMPANY OF THE HEBREW UNIVERSITY OF JERUSALEM LTD., Jerusalem (IL); LUDWIG-MAXIMILIANS-UNIVERSITÄT MÜNCHEN, Munich (DE)

(72) Inventors: Eitan Lerner, Rehovot (IL); Thorben Cordes, Gauting (DE); Yair Razvag, Maon Avigail (IL); Paz Drori, Nordia (IL); Gabriel Moya, Munich (DE)

(73) Assignees: YISSUM RESEARCH DEVELOPMENT COMPANY OF THE HEBREW UNIVERSITY OF JERUSALEMLTD., Jerusalem (IL); LUDWIG-MAXIMILIANS-UNIVERSITÄT, Munich (DE)

( * ) Notice: Subject to any disclaimer, the term of this patent is extended or adjusted under 35 U.S.C. 154(b) by 536 days.

(21) Appl. No.: 18/276,666

(22) PCT Filed: Feb. 11, 2022

(86) PCT No.: PCT/IB2022/051228
§ 371 (c)(1),
(2) Date: Aug. 10, 2023

(87) PCT Pub. No.: WO2022/172208
PCT Pub. Date: Aug. 18, 2022

(65) Prior Publication Data
US 2024/0142460 A1 May 2, 2024

Related U.S. Application Data

(60) Provisional application No. 63/148,181, filed on Feb. 11, 2021.

(51) Int. Cl.
*G01N 33/58* (2006.01)
*G01N 15/14* (2006.01)
*G01N 15/1404* (2024.01)

(52) U.S. Cl.
CPC ....... *G01N 33/582* (2013.01); *G01N 15/1404* (2013.01); *G01N 15/1484* (2013.01)

(58) Field of Classification Search
None
See application file for complete search history.

(56) References Cited

U.S. PATENT DOCUMENTS 5,716,852 A * 2/1998 Yager ................. G01N 30/0005
436/180
2012/0050734 A1* 3/2012 Wennmalm ........ G01N 21/6458
356/318

* cited by examiner

*Primary Examiner* — Ann Montgomery
(74) *Attorney, Agent, or Firm* — Daniel J. Swirsky; AlphaPatent Associates Ltd

(57) ABSTRACT

Systems and methods that allow optical detection of nanoparticles according to size and interaction with specific antibodies. Using a biological sample combined with fluorescent dyes and fluorescently labeled antibodies, implementations of the disclosed system allow for detection of >100 particles having diameters as low as 100 nm in under 10 minutes. The detection mechanisms combine confocal detection of particles in microfluidic flow devices. Concentrating the sample using hydrodynamic focusing allows detection of particles having concentrations as low as $10^4$ particles per mL of the sample. These capabilities allow for the detection, identification, and quantitation of viruses from bodily fluids such as saliva, where biologically relevant virus concentrations of potentially infected subjects are within the range of $10^3$-$10^7$ particles/mL. The system and methods comprise a 'flow virometer' providing rapid, direct feedback regarding the existence of specific viruses in a biological sample and serves as a technological basis for commercial products.

25 Claims, 7 Drawing Sheets

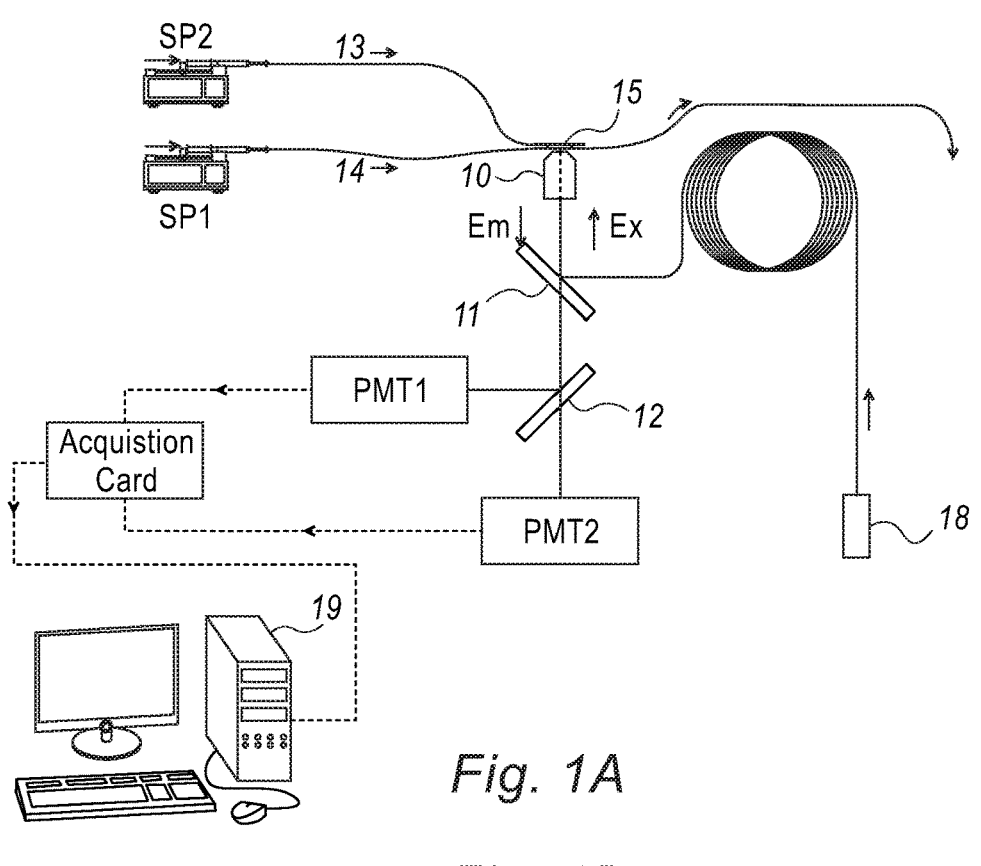
*Fig. 1A*
*Fig. 1B*
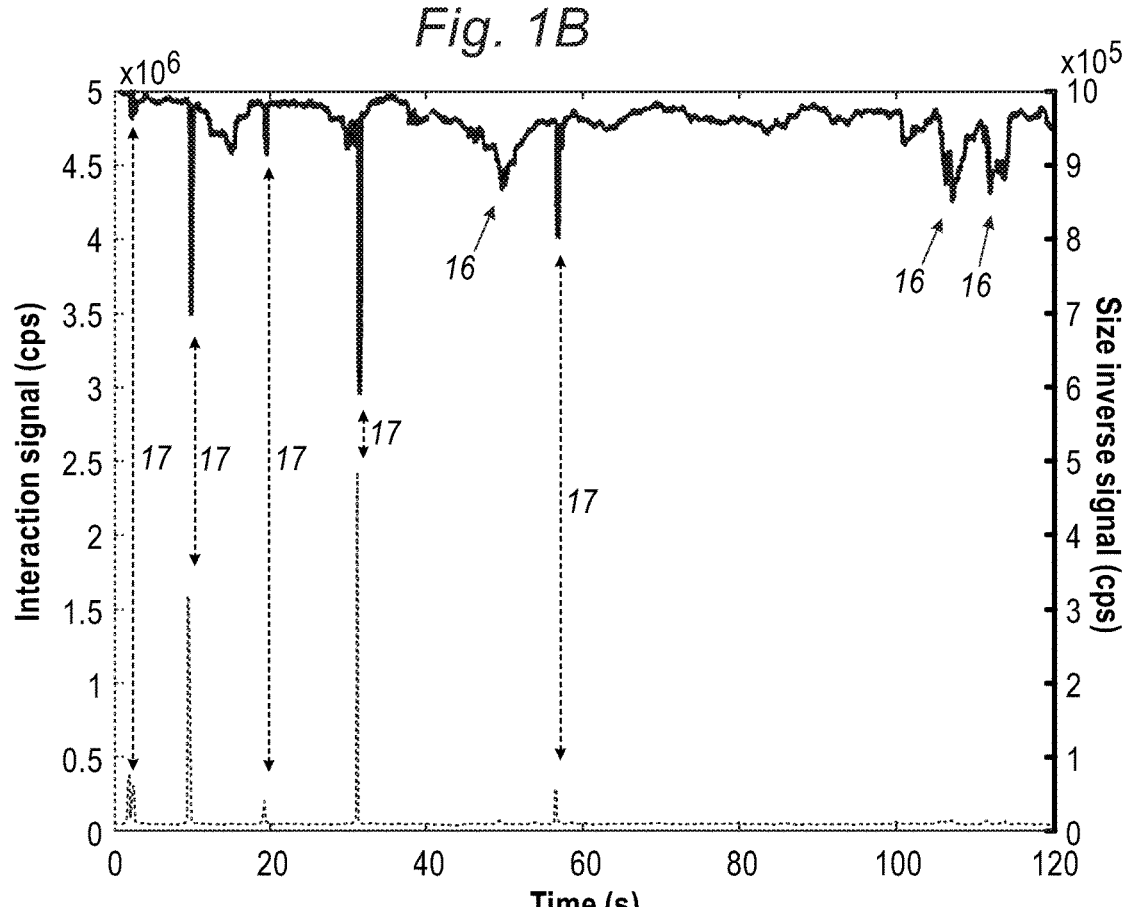

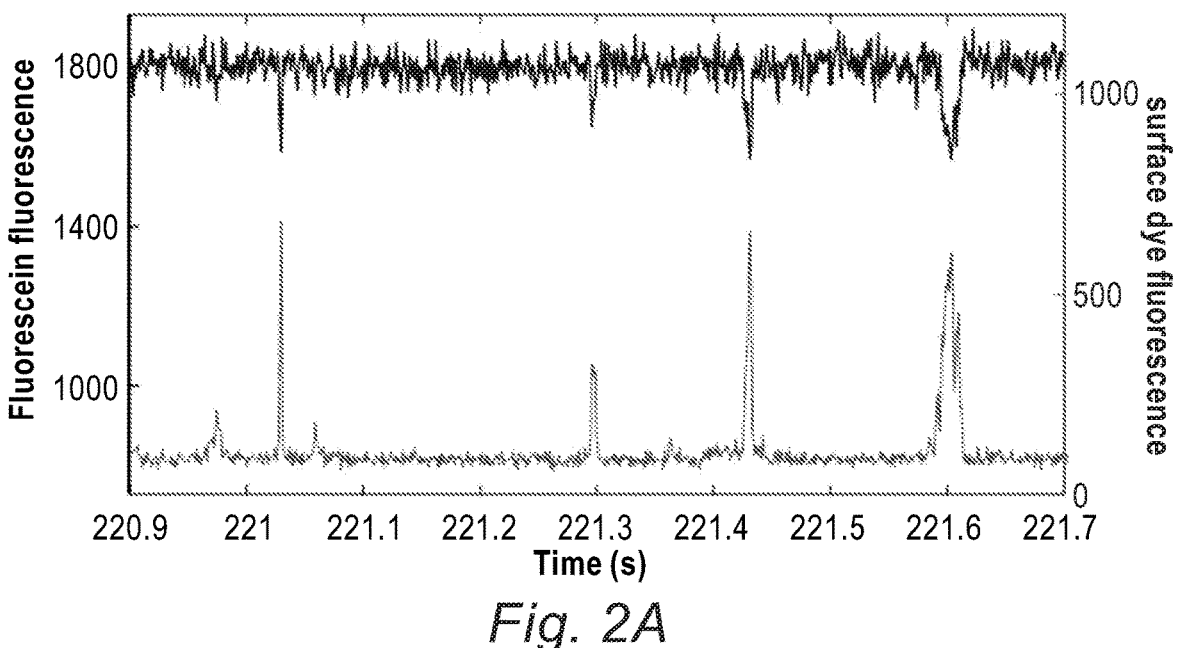
*Fig. 2A*
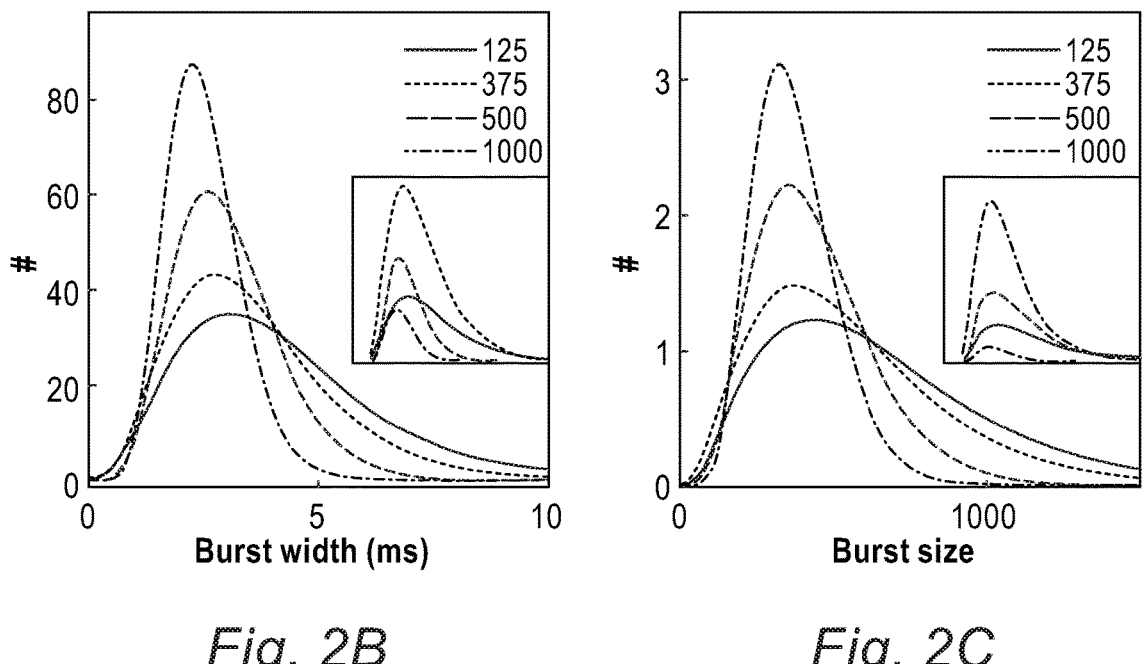
*Fig. 2B*          *Fig. 2C*

FLOW VIROMETER FOR RAPID DETECTION OF INTACT VIRUSES

FIELD OF THE INVENTION

The present invention relates to the field of development of a device for the specific, sensitive and rapid detection of specific intact viruses.

BACKGROUND

Mainstream diagnostics of viruses rely on polymerase chain reaction (PCR), a technique which is accurate and sensitive. However, the process is laborious and relies heavily on resources that may be expensive, limited, or difficult to obtain. In a time when rapid diagnosis could identify infected individuals, and thus prevent transmission of infection to unsuspecting third parties, a rapid screening procedure for specific viral infection is needed.

The current method of viral detection with the highest specificity is DNA/RNA-based, useful when viral particles are found in low amounts. PCR or RT-PCR allows amplification of the viral signal using primers specific to viral DNAs or RNAs. For nucleic acid detection, the lower the amount of initial DNA/RNA, the more cycles of PCR/RT-PCR are required to amplify the signal to a detectable range. However, the more cycles of amplification required, the longer the procedure and the greater the chance for false positive results.

As an example, most confirmed COVID-19 patients can be identified as being positive for the virus after 35-40 cycles of PCR amplification of a sample. However, over time it has become clear that many of these individuals receive a negative result upon re-examination shortly thereafter, thus leading to a significant incidence of false positive results. In some cases, a first test result is negative and a subsequent sample tests positive. Other means of confirming infection rely on past exposure and serological evidence of a prior immune system response. These and other indirect methods of detection do not necessarily reflect the current viral load.

Documents relevant to the field include:

K. K.-W., Tsang, O. T.-Y., Leung, W.-S., et al. "Temporal Profiles of Viral Load in Posterior Oropharyngeal Saliva Samples and Serum Antibody Responses during Infection by SARS-CoV-2: An Observational Cohort Study". Lancet Infect. Dis. 2020, 20 (5), 565-574.

Wennmalm, S., Thyberg, P., Xu, L., et al. Inverse-Fluorescence Correlation Spectroscopy. Anal. Chem. 2009, 81 (22), 9209-9215.

Wennmalm, S., Widengren, J. "Inverse-Fluorescence Cross-Correlation Spectroscopy". Anal. Chem. 2010, 82 (13), 5646-5651.

International Patent Application publication WO 2010/119098 to S. Wennmalm, et al., for "Inverse-Fluorescence Correlation Spectroscopy".

Yang, A.-S., Hsieh, W.-H. "Hydrodynamic Focusing Investigation in a Micro-Flow Cytometer. Biomed. Microdevices" 2007, 9 (2), 113-122.

Kelly, M. D. E.-R. T. "Hydrodynamic Focusing in Microfluidic Devices", Intech Open: Rijeka, 2012, Ch. 2.

Hong, S., Tsou, P.-H., Chou, C.-K., et al. "Microfluidic Three-Dimensional Hydrodynamic Flow Focusing for the Rapid Protein Concentration Analysis". Biomicrofluidics 2012, 6 (2), 24132.

Black, J. A., Hamilton, E., Hueros, R. A. R., et al. "Enhanced Detection of Single Viruses On-Chip via Hydrodynamic Focusing". IEEE J. Sel. Top. quantum Electron. Publ of IEEE Lasers Electro-optics Soc. 2019, 25 (1).

J J Mittag, J O Rädler, J J McManus. "Peptide Self-Assembly Measured Using Fluorescence Correlation Spectroscopy". Methods Mol Biol. 2018, 1777:159-171.

In an age of rapid global spread of viral infections, there exists a need for a means of rapid, simple, and inexpensive method of screening the population, which overcomes at least some of the disadvantages of prior art systems and methods. Such an initial screening step could be useful before deciding whether to employ more sensitive and time-consuming PCR-based or serological testing.

The disclosures of each of the publications mentioned in this section and in other sections of the specification, are hereby incorporated by reference, each in its entirety.

SUMMARY

The present disclosure describes new exemplary systems for sensitive and rapid detection of virus particles in human samples using a system that could be termed a 'flow virometer' which performs inverse fluorescence cross-correlation spectroscopy (iFCCS) of particles in laminar flow inside a microfluidic device. A currently used technique is based on inverse fluorescence correlation spectroscopy (iFCS) as described in the above mentioned International Patent Application, Publication WO 2010/119098 to S. Wennmalm, et al., wherein confocal-based fluorescence is used to detect diffusing particles or biomolecules in solution or in cells. However, until development of the techniques, developed and described herewithin below, previously available direct or indirect fluorescence-based detection techniques were unsuitable for detection of intact viruses because of the low concentration of viral particles in naturally occurring biological samples. Available fluorescence-based detection of intact virus particles is both indirect, using an estimate based on the intensity of fluorescence staining, which limits the accuracy, and requires a certain quantity of particles in the sample for detection, a limitation which significantly reduces the practical application to clinical samples.

The technology of the present disclosure solves the problem of rapid optics-based counting of sub-microscopic particles such as viruses. The proposed system enables counting of the order of 100 particles such as viruses, with diameters greater than 50 nm, at concentrations as low as $10^3$ particles/mL, within a time of less than 10 minutes. It is expected, however, that even greater sensitivity is achievable with improvement of the detection system components, and the cited sensitivity is not intended to limit the capabilities of the presently described exemplary systems. For reference, the SARS-CoV-2 virus has been measured to range in diameter from 60-140 nm, and the influenza virus is estimated to be in the range of 70-120 nm. The selection of the nominal criterion of the detection of 100 viral particles within 10 minutes as the relevant parameter is based on the minimal number of particle detection events needed to reach a predetermined level of statistical significance, in a time frame expected to be relevant for rapid clinical diagnosis. These parameters may be adjusted for specific circumstances and applications as needed for a required degree of sensitivity.

Implementations of the current methods and systems make use of a flow virometer that facilitates specific detection of intact virus particles and rapid counting thereof. The microfluidics-based flow-virometer device utilizes hydrodynamic focusing of the liquid sample to concentrate the stream of particles and to provide more sensitive results than is possible with a freely flowing sample. The constraining effect of the sheath flow is achieved by keeping the sheath-to-analyte flow rate ratio high enough to attain the desired concentration of the analyte flow, but not so high as to cause turbulences. In a freely flowing sample, particles flow through a channel with a cutoff area much larger than that of the laser focus. As a result, most of the particles do not flow through the laser focus, and hence are not detected. Hydrodynamic focusing helps decrease the cutoff area of the flowing stream of particles, which increases the number of particles that will flow through the laser focus. Particle size is difficult to detect accurately without directed flow. Previous means of particle detection in a directed flow have been developed, such as a Coulter counter, in which an electrolyte containing the cells travels through a small aperture having an electric field applied through it. The count is achieved by observing the changes in current detected as a cell travels through the aperture, replacing the electrolyte otherwise therein. Flow cytometry has been used to count cells, bacteria and even viruses; however, the required equipment is expensive and using it to count viruses relies solely on specific antibody labeling, and not on the viral particle sizes. While hydrodynamic focusing is used in flow cytometers or Coulter counters for determining the size of bacteria or cells, the system of the present disclosure differs in that the hydrodynamic focusing is applied to a microcopy arrangement of iFCCS spectroscopy, enabling detection of particles two to three orders of magnitude smaller than human cells.

The iFCCS-based detection of coincident signals from two detection channels involves both a negative signal, a "dip" in the stable fluorescence signal from high concentration of free dye in solution, the dip arising from the exclusion of a fraction of the dyes by the particle to be detected, and a positive signal, a "burst", arising from the target specifically labeled with a detectable molecule: for example, an antibody, nanobody, peptide, or molecule targeting the particle's surface proteins. The present disclosure describes an extension to the iFCCS approach, identifying one particle at a time, applied to a hydrodynamically focused narrowed sample flow, enabling accurate and specific recognition and quantitation of previously undetectable particles in biological samples. Exemplary implementations of the present disclosure thus provide a novel confocal microscopy-based detection scheme for small particles such as viruses present at low concentrations in biological samples, either alone or in the presence of antibodies, in a time frame that may be useful in clinical detection scenarios. In exemplary implementations, sample volumes of less than 20 μL in laminar flow can be tested in a simple disposable microfluidic channel.

The bio-detection method uses confocal optical imaging to identify and count intact virus particles in a laminar flow microfluidic cell. Two fluorescent dyes, each having a specific excitation and emission wavelengths, are used. A first dye, such as fluorescein, is added to the sample flow at sub-millimolar concentrations, creating a signal corresponding to the fluorescence of the free-flowing dye. A second fluorescent dye, such as rhodamine 800, is used to label antibodies specific for the virus whose detection is sought. The antibody-tagged dye, will bind to antigens on the surface of the virus, should the sample contain the virus being sought. By bringing the focal spot of the laser inside the flow mixture, the laser excites the free dyes (fluorescein) and produces a constant background fluorescent signal, which, by using a sufficiently high concentration of added dye, will provide a constant background signal having reasonably low noise fluctuations or disturbances. When a particle passes through the focal volume of the laser, the particle reduces the level of free dyes in the focal volume by an amount proportional to the particle volume, which leads to a dip in the constant fluorescent signal. The larger the particle, the greater the dip. In addition, the fluorescence of the antibody is detected directly in a different spectral bandwidth to that of the free-flowing dye, using a separate detector. If a particle flowing through the focused beam has antibodies attached to it, a signal dip will be recorded by the free-flowing dye detector, and simultaneously a signal burst will be recorded by the second detector. Such a coincident detection is recorded as one specific particle detection event.

The specificity of particle detection in the sample is based on changes in both the two fluorescence-based signals, each having different excitation and emission wavelengths from the other. In this example, the first change may be a specific decrease in the fluorescein signal, known as the "dip" signal, the level of the dip being indicative of the passing particle size. The second change may be a rhodamine 800 "burst", indicating specific binding of dye-labeled antibodies or receptors to the surface of the virus or other target. By recording simultaneous signals in both the fluorescein (green) and rhodamine 800 (red) spectral detection channels, coincident events are detectable in the two signal output traces.

The output provides two coinciding signals, i.e., the 'dip' that is proportional to the void volume of the virus, and the 'burst' that indicates a viral particle bound to an antibody. The basis of identifying a virus comes from recording a dip and a burst at the same time, indicating a virus passing through the laser focal volume with an antibody bound to it. The specificity of detecting a particular species of virus comes from the binding of antibodies specific to its surface proteins, and from determining that the particle size is compatible with that virus. Switching between detection of one virus to another does not depend on the apparatus, but only on the mixture of dyes and antibodies in the solution that are mixed with the specimen sample. Quantization of detection events, indicating viral particles, is achieved by counting the number of coinciding "dip" and "burst" events as a function of time. Individual dip events that are not coincident with a burst, are indicative of particles of certain sizes that were not labeled by the antibodies, and therefore might be indicative of particles other than the virus being sought, or particles of the sought-after virus to which antibodies did not bind.

The magnitude of the dip, is directly proportional to the volume of the nanoparticle passing through the excitation volume. If the volume of the nanoparticle is smaller than a given value, relative to the volume of the effective excitation volume, its contribution to the decrease in the background fluorescein signal can be comparable to the amplitude of the noise around the average of the fluorescein signal. In that case, the burst of fluorescence from the other channel (a fluorescence signal from the antibody) can be used for the detection of the specific nanoparticle, but without knowing what its size is, due to the lack of an observable dip in the fluorescein signal. With simple PMT detectors, the smallest nanoparticle that is observed as a clear dip in the signal, due to it passing through the effective excitation volume, is a spherical particle with a diameter of 100 nm. For smaller nanoparticles, even if no dip is detected, the burst of fluorescence from the other channel (the antibody channel) is indicative of a labeled particle, and it can be used to identify the nanoparticle, without knowing what its size is, which would otherwise be known from the dip in the background fluorescence signal.

Using this method, accurate detection of specific viruses and virus-like particles can be achieved, with low rates of false positive and false negative results. At least 100 virus-like particle detection events can be achieved in at most 10 minutes for biologically relevant virus concentrations in saliva at concentrations as low as $10^3$-$10^4$ particles/mL by use of hydrodynamic focusing, which improves the microfluidics to facilitate the sensitivity required for detecting low viral loads. The system is adaptable for bio-detection of many viruses and virus-like particles as well as other biological particles in the 50-1000 nm diameter range.

With respect to the limit of resolution of the method, in implementations using confocal imaging, the resolution is constrained by Abbe's diffraction limit and the resolving power of the objective lens to distinguish distinct particles. If immobilized dye-labeled particles having different diameters less than 250 nm were detected by confocal imaging, every particle would be represented by a single pixel. In a free-flowing sample detecting unlabeled particles in a high concentration of free dye, the diffraction limit of the light applies to the dyes rather than to the particles. In one exemplary apparatus, the laser focal volume can be approximated by a cylinder of approximately 300 nm diameter by 1,000 to 1,500 nm height, filled with light of specific wavelengths. Applying a sample flowing through the laser focal volume under laminar flow conditions, a viral particle having 100-120 nm diameter, passing through the laser focal volume at constant velocity, creates a temporary void in the dyes inside the focal volume cylinder, and hence reduces the dye molecules by a fraction equal to the ratio of the viral particle volume to the total laser focal volume. Based on the above calculations, implementations of the disclosed methods ensure that the signal-to-noise ratio is high enough that even a 0.1% decrease in dye concentration, i.e., when the virus volume is 0.1 percent of the focal volume, will be detectable by detectors having the required sensitivity. This would apply for the case of a virus having a diameter of 0.1 μm and the focal volume having a height of 1.5 μm and a diameter of 0.3 μm.

In some implementations, techniques such as stimulated emission depletion (STED) may be used to increase the limits of optically defined spatial resolution. Increasing the sensitivity of detection improves temporal resolution, by the resulting higher photon detection efficiency, smaller detector dead times, higher light saturation thresholds and low dark counts. In implementations in which sample immobilization is achievable, photo-activated localization microscopy (PALM), and direct stochastical optical reconstruction microscopy (dSTORM) may be used to increase the sensitivity of the method. Using these implementations, it is believed that it would be possible to detect more than 1,000 particles in under 5 min in samples having concentrations of as low as $10^3$ viruses/ml.

Various implementations of the methods of the present disclosure may use other techniques and apparatus to accomplish the small effective excitation volume (~$1\times10^{-15}$ L) reached by the combination of tightly focused laser beam, pinhole and high sensitivity point detectors that are typically, but not essentially, part of a commercial confocal microscope. The dyes, proteins, antibodies, and/or nanobodies used in various implementations of the system may be free in solution or immobilized via attachment to the microscope slide or coverslip surface, using high-affinity molecular linkages such as those between biotin and avidin. If the proteins, antibodies, and/or nanobodies used for specific identification of the virus are surface-immobilized, an attenuation in the virus particle flow may be detectable using the present methods, or by other imaging methods. To avoid dye penetration into viral particles, larger molecular dyes, such as quantum dots, dye-labeled beads or dye-labeled proteins (e.g. bovine serum albumin; BSA), may be used to minimize dye penetration and maximize the size of the inverse dip signals.

There is therefore provided according to a first exemplary implementation of the present disclosure, a method for detection of a specific nanoparticle in a biological sample, comprising:

a) providing an analyte comprising: (i) at least a portion of the biological sample, (ii) a first dye having a first fluorescence wavelength, the first dye being able to link to a first member of a pair-forming molecular group, the first member having specific affinity for a second member of the pair-forming molecular group, the second member being attachable to the specific nanoparticle, and (iii) a second dye having a second fluorescence wavelength;

b) narrowing a flow containing the analyte through a microfluidic device adapted to generate a hydrodynamically-focused laminar flow, the microfluidic device being positioned in the focal volume of a laser capable of exciting the first dye wavelength and the second dye wavelength; and c) detecting changes in the intensities of a first signal corresponding to the level of fluorescent emission from the first dye and a second signal corresponding to the level of fluorescence emission from the second dye, the emissions resulting from excitation of the dyes by the laser, wherein a decrease in the level of the second signal with a simultaneous increase in the level of the first signal, indicates passage of a single, specific nanoparticle.

In some exemplary implementations of the disclosed methods, the specific nanoparticle may be a virus, a virus-antibody complex, an exosome, or another nanoparticle having a diameter greater than 100 nm. The biological sample may comprise any of sputum, serum, cerebral spinal fluid, urine, or feces, whether directly applied to the microfluidic chamber or processed prior to application.

An indication of the volume of the detected specific nanoparticle may be obtained by measuring the extent of the decrease in the level of the second signal occurring with a simultaneous increase in the level of the first signal, or by the duration of the second signal occurring with a simultaneous increase in the level of the first signal.

In some implementations, the hydrodynamic focusing is capable of concentrating the flow by a factor of at least 1,000, or even at least 10,000, relative to unconstrained laminar flow in a constant cross-section microfluidic device without hydrodynamic focusing. The microfluidic device may comprise a multi-channel chip mounted on a slide of a confocal microscope. The method may further comprise the use of hydrodynamic focusing inside the microfluidic device to accomplish the laminar flow in the microfluidic device, and may further comprise the step of counting over a predetermined time duration, the number of events showing a decrease in the level of the second signal occurring with a simultaneous increase in the level of the first signal, to provide a quantization of the specific nanoparticles.

The specific nanoparticle to be detected may be determined by selection of the first dye, according to its ability to link to a first member of the pair-forming molecular group. In some implementations, the first member of the pair-forming molecular group is an antibody, and the second member of the pair-forming molecular group is an antigen, wherein the antigen is a surface molecule on the nanoparticle to be detected, and the nanoparticle is a virus. The antibody may comprise any of: a non-human antibody, a humanized antibody, a human antibody, a chimeric antibody, a bispecific antibody, and an antibody fragment comprising at least the antigen-binding fragment of an antibody. The antigen-binding fragment of an antibody may refer to any of: antibody fragment selected from the group consisting of: Fab, Fab', F(ab')2, Fd, Fd', Fv, dAb, isolated CDR region, single chain variable region (scFV), single chain antibody (scab), "diabodies", and "linear antibodies".

In other implementations, the first member of the pair-forming molecular group is a lectin, and the second member of the pair-forming molecular group is a glycoprotein; or the first member of the pair-forming molecular group is a receptor, and the second member of the pair-forming molecular group is a ligand that binds specifically to the receptor; or the first member of the pair-forming molecular group is an enzyme, and the second member of the pair-forming molecular group is a substrate whose reaction is catalyzed by the enzyme; or the first member of the pair-forming molecular group is an RNA or DNA nucleic acid sequence, and the second member of the pair-forming molecular group is either a complementary RNA or DNA sequence, or a DNA binding protein aptamer. The first dye may be a fluorophore having specific excitation and emission wavelengths, and the second dye a fluorophore having specific excitation and emission wavelengths that differ from those of the first fluorophore.

In some implementations, the method is capable of detecting 100 of the specific nanoparticles in less than 10 minutes, and the detection capability is attainable with less than 20 µL of the biological sample at concentrations as low as $1 \times 10^4$ particles/mL. The laminar flow may be generated by mixing the analyte flow with two flanking sheath flows joining the analyte flow at a defined angle.

According to yet further implementations disclosed in this application, there is further provided a system for detection of a specific nanoparticle in a biological sample that comprises:

(i) a confocal optical system having a laser illumination source;

(ii) a microfluidic device positioned in the focal volume of the confocal optical system, and adapted to generate a hydrodynamically focused laminar flow of an analyte passed therethrough, the analyte comprising a portion of the biological sample, a first dye emitting a first fluorescence wavelength on excitation by the laser illumination source, and a second dye emitting a second fluorescence wavelength on excitation by the laser illumination source; and (iii) a correlation optical arrangement for outputting as a function of time, a first signal arising from the first fluorescence emission of the first dye, and a second signal arising from the second fluorescence emission of the second dye, wherein the first dye is selected to bind to a first member of a pair-forming molecular group, the first member having specific affinity for a second member of the pair-forming molecular group, and the second member being attachable to the specific nanoparticle, such that detection by the correlation of a simultaneous decrease in the level of the second signal with an increase in the level of the first signal, indicates passage of a single specific nanoparticle.

In the above described system, the confocal optical system may comprise a dichroic mirror adapted to transmit light emitted from the flow through the microfluidic device having the wavelength of one of the fluorescent emissions, and to reflect light emitted from the flow through the microfluidic device having the wavelength of the other of the fluorescent emissions.

The specific nanoparticle may be any one of a virus, a virus-antibody complex, an exosome, or another nanoparticle having a diameter greater than 100 nm. The biological sample may comprise any of sputum, serum, cerebral spinal fluid, urine, or feces. The extent of the decrease in the level of the second signal occurring with a simultaneous increase in the level of the first signal, provides an indication of the volume of the detected specific nanoparticle. A duration of the second signal occurring with a simultaneous increase in the level of the first signal may be used to provide an indication of the volume of the detected specific nanoparticle. Hydrodynamic focusing may be used to accomplish the narrowed laminar flow in the microfluidic device, which may comprise a multi-channel chip mounted on a slide of a confocal microscope.

The system may further incorporate the step of counting over a predetermined time duration, the number of events showing a decrease in the level of the second signal occurring with a simultaneous increase in the level of the first signal, to provide a quantization of the specific nanoparticles by selection of the first dye, according to its ability to link to the first member of the pair-forming molecular group. The first member of the pair-forming molecular group may be an antibody, and the second member of the pair-forming molecular group an antigen. The first dye may be a fluorophore having specific excitation and emission wavelengths, and the second dye a fluorophore having specific excitation and emission wavelengths that differ from those of the first fluorophore. The laminar flow may be generated by mixing the analyte flow with two flanking sheath flows joining the analyte flow at a defined angle, and that angle may advantageously be a right angle or close to a right angle.

BRIEF DESCRIPTION OF THE DRAWINGS

The presently claimed invention will be understood and appreciated more fully from the following detailed description, taken in conjunction with the drawings in which:

FIGS. 1A and 1B show the arrangement of sample analysis and detection using fluorescence microscopy, and a sample result showing the output signals;

FIGS. 2A-2G show sample data obtained using an implementation of the disclosed methods;

FIG. 7 illustrates how filtering the dips that are cross-correlated with bursts is performed; and.

DETAILED DESCRIPTION

Figure 2D:
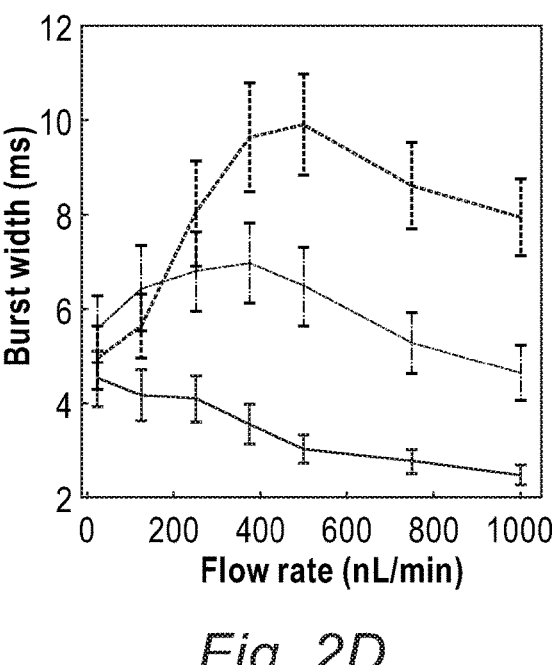

Reference is now made to FIGS. 1A-1B, which illustrate schematically, elements and results of an exemplary apparatus for implementation of the disclosed methods. In FIG. 1A, there is shown an exemplary optical setup for analyzing a sample taken from a subject, for the rapid detection of specific viruses carried by the subject. The sample, often taken from the oral cavity of the subject, is generally dipped in a solution to release any virus particles, a fluorescent dye and a nanoparticle-specific dye-labeled antibody are added to the solution, before it is introduced as the analyte flow 14 into a microfluidic chamber 15, typically by injection with a syringe pump SP1. A sheath flow 13 of liquid containing a transparent aqueous solution, is injected into the sheath flow channels of the microfluidic chamber 15 using syringe pump SP2. Details of a typical microfluidic chamber are given hereinbelow in FIG. 3A. The sample is subjected to fluorescence imaging using a confocal-microscopy based setup with the input illumination focused on the sample in the microfluidic chamber 15, at the center of the hydro-dynamically-focused stream of nanoparticles. The excitation laser 18 sends its illumination marked Ex, down a fiber optical transmission path FO, and by reflection in a dichroic mirror 11, into the objective optics 10, of the confocal microscopy arrangement and produces a focal volume within the analyte flow channel of the microfluidic chamber 15. As the analyte fluid flows, any viral particles or virus-antibody particles are detected by analyzing the change in the level of each fluorescence emission Em at the characteristic wavelength of each fluorescing dye, as they pass individually through the laser focal volume, as described below. The emitted fluorescent light Em, passes to a second dichroic mirror 12, where the fluorescence from two dyes in the analyte flow, free dye and a nanoparticle-specific dye-labeled antibody are split up, one going to the PMT1 detector and the other going to the PMT2 detector. The signals from the two detector channels are input into the acquisition card, where the data is analyzed and the output transferred to the computer system 19 for display, manipulation, storage, or export to remote handling or storage. The optical system of FIG. 1A shows only the essential elements of the optical setup, and in addition there may also be a concentrating lens, a pinhole at the focus of the emission beam and another concentrating lens to re-collimate the emission beam between dichroic mirrors 11 and 12, and narrow bandpass filters in front of each of the PMT detectors.

In FIG. 1B, the output signals of a representative analysis are shown. The x-axis shows time in seconds. The left y-axis shows the interaction signal in counts per second (cps). The height of the interaction signal is indicative of the number of antibodies that interacted with the proteins on the virus-like particle surface. The right y-axis shows the inverse signal, shown as a dip in the measured signal, in cps. Particles with large volumes yield large dips, while smaller particles yield smaller dips. Large particles without surface interaction show smaller magnitude signals having a longer duration of up to several seconds, as shown in the three signal dips 16 without surface interaction on the right half of the graph of FIG. 1B. The longer duration is the effect arising from the increased time that a larger particle takes in crossing the focused laser beam, and hence the longer time that the fluorescence signal is reduced. The magnitude of the interaction signal is directly proportional to the amount of surface protein targets on a particle, the amount of added antibodies and the binding affinities of these antibodies to the surface protein targets. These particles without surface interaction are not labeled by antibodies and represent particles having diameters>100 nm, and are other than the particles sought, since antibodies have not bound to their surface proteins. These signals constitute 'noise', as these particles are not necessarily indicative of a specific viral species. An exemplary implementation of the system combines detection of both antibody interaction and particle size signatures by positioning the tight focus of a laser beam into a mixture in laminar flow inside a microfluidic channel. The mixture may include high concentrations of free green fluorescent dye ($\geq 100$ $\mu$M fluorescein), and picomolar (pM) concentrations of red fluorescently-labeled antibodies targeting a specific virus capsid protein.

When the sample passing the laser focal volume is free of virus, the high concentration of free dye produces a stable high fluorescent signal with low noise, reflecting the average amount of free green dye in the sample as it flows past the laser focal volume. When a virus particle traverses the laser focal volume, the amount of free green dye is reduced by the volume of the virus particle. This results in a temporary 'dip' in the stable fluorescence signal detected by one detector, termed inverse bursts. When applied without the application of laminar flow, this detection scheme is called inverse fluorescence correlation spectroscopy (iFCS). To regularize the size and duration of the inverse bursts per each particle size and to minimize the signal variance due to diffusion, the presently disclosed apparatus measures particles in laminar flow. The size and duration of inverse bursts scale proportionally with the size of the particles. Simultaneously, a second detector monitors fluorescence bursts arising from fluorescently labeled antibodies traversing the laser focal volume. If both virus particles and dye-labeled antibodies are dilute (less than 100 $\mu$M in the region of the microfluidics channel probed by the laser focal volume), the coincident detection of an inverse burst, together with the antibody-dependent burst, as indicated 17 in FIG. 1B on the left side of the graph, is equivalent to the detection of one target particle. Exemplary methods of the current disclosure discriminate particles of different sizes in laminar flow, which is more accurate and allows detection of lower concentrations of samples as opposed to tracking freely-diffusing particles. A combination of the "dip" and "burst" effect increases the specificity of the detection.

Figure 2E:
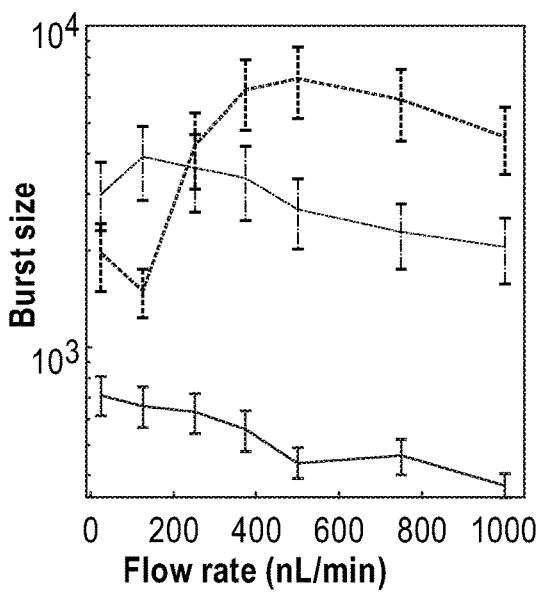
Figure 2F:
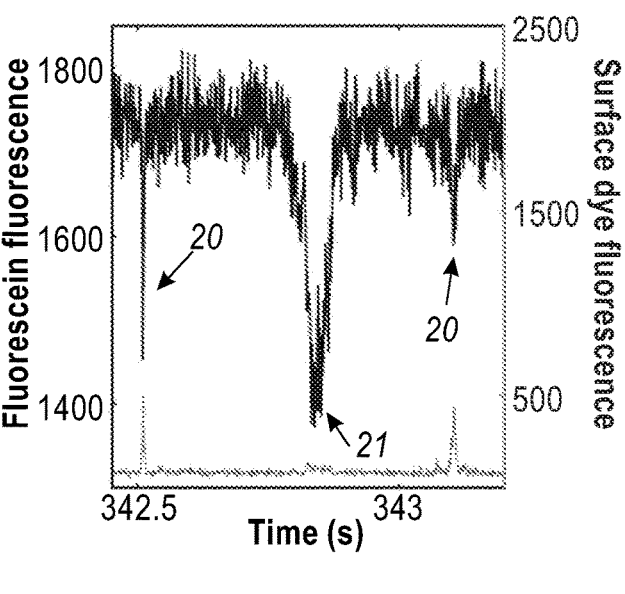
Figure 2F:
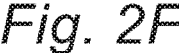
Figure 2G:
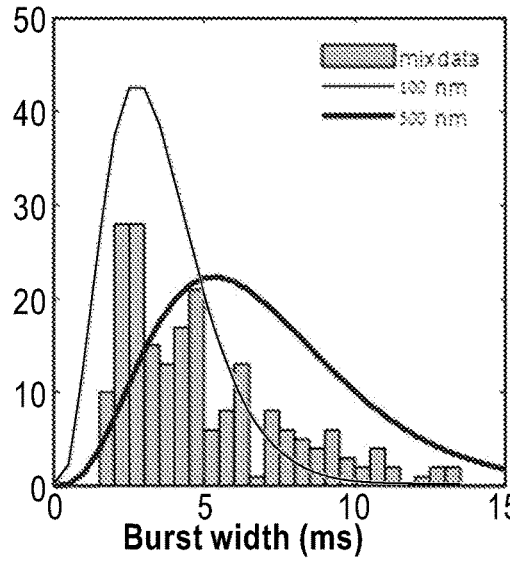

Reference is now made to FIGS. 2A-2G, illustrating an exemplary implementation of the above-described methods on fluorophore-labeled nanobeads. FIG. 2A shows a representative output of an experiment with 100 nm dye-labeled beads flowing at a flow rate of 375 nL/min. The elapsed time is shown on the x-axis and the duration of the output illustrated is 0.8 seconds, from 220.9 to 221.7 seconds of recorded observation. On the left y-axis is shown fluorescence of the free green dye having a specific excitation and emission wavelength, represented by the upper trace. On the right y-axis the fluorescence of the dyes attached to the surface of the bead is shown, having excitation and emission wavelengths different than those of the free green dye, represented by the lower trace. The figure demonstrates the capability of detecting nanobeads of 100 nm diameter, a size on the scale of many viruses. The upper trace represents the "dip", which is due to nanobead exclusion of the free dyes in the passing solution, and the "bursts" in the lower trace represent the positive fluorescent signal from dye-labeled nanobead. The coincident detection of both signals at the same time ensures a positive virus signal, as counts accumulate with time. Dips in the fluorescence signal of the free green dye (fluorescein) are represented by inverse bursts, and these coincide with the positive bursts of bead surface dye fluorescence on the lower trace. In FIGS. 2B and 2C are shown the distribution of burst durations, widths, and sizes, respectively, at flow rates of 1,000, 500, 275, and 125 nL/min, and as captured by fitting to gamma distributions. The insets represent normalized curves for both graphs. In FIGS. 2D and 2E is shown the mean and standard deviations of burst durations and sizes, respectively, at different flow rates for beads with diameters 1,000 nm (finely dashed line), 500 nm (coarsely dashed line) and 100 nm (full line). FIG. 2F shows a sample of a recording trace arising from a mixture of 100 nm dye-labeled beads and 500 nm unlabeled beads flowing at a rate of 375 nL/min. The arrows 20 indicate coincident detections of the 100 nm beads. The major inverse burst 21 not accompanied by a burst of bead surface dye fluorescence arises from the 500 nm unlabeled bead and represents a particle with a volume larger than the 100 nm nanobeads, not carrying the specific targets of interaction, and hence a particle of a different type that may be found in a biological sample. The burst width of 100 nm diameter nanobeads is smaller than that of 500 nm diameter nanobeads, owing to the shorter time it takes the smaller beads to traverse the dimensions of the confocal volume, which may typically comprise a passage having a width of ~300 nm and height of 1.0-1.5 μm. The dip magnitude, i.e. the maximal decrease in the constant fluorescence signal, is proportional to the volume that excludes the maximal amount of free green dyes from the confocal volume. Both burst width (duration), corresponding to the time taken for the particle to pass the laser focal volume (FIG. 2B), and burst depth, corresponding to particle volume (FIG. 2C), also depend on the flow rate, in a predictable and calibratable fashion, as shown in FIGS. 2D and 2E. The coincident detection of dips & bursts allows for a higher degree of accuracy by confirming the detection based on both the particle size and the specific-interaction fluorescence. FIG. 2G shows an exemplary histogram of burst widths from all coincident bursts, compared to the width probabilities recorded at a flow rate of 375 nL/min for beads of a single diameter, either 100 nm (the left hand sharper peak) or 500 nm (the right hand flatter peak). These results may be used to calibrate the system and provide an estimate of particle size based on standard curves.

Figures 3A, 3B, 3C:
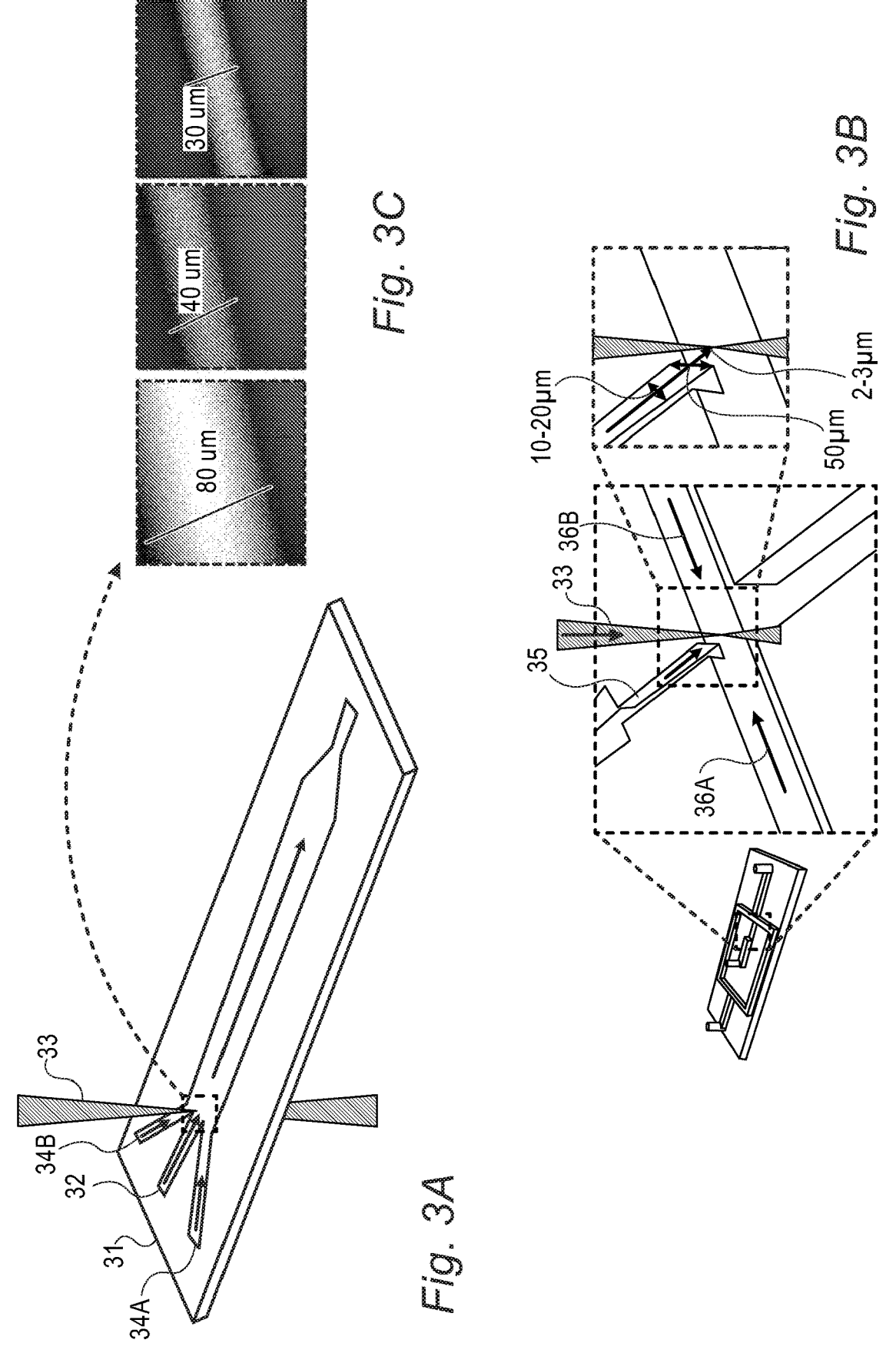
FIGS. 3A-3C show exemplary flow meters and typical dimensions of fluorescent fluid flow using hydrodynamic focusing.

Reference is now made to FIGS. 3A-3C, showing an example of the apparatus and methods that could be used for performing hydrodynamic focusing in flow virometry. In FIG. 3A is shown a 3-in-1 commercial microfluidic channel, supplied by Ibidi GmbH of Gräfelfing, Germany, with the confocal volume of the laser beam 33 positioned right after a short section of hydrodynamic focusing, using a 3-in-1 microfluidics channel 31. The sample analyte flows through the central channel 32 from the left at a given flow rate, with sheath flow on both side channels 34A, 34B with constant flow rates at least ten times higher than the analyte flow rate. The sheath flow focuses the stream of analyte, causing an increased volume of analyte to flow past a point in the microfluidic device at which the laser focal volume is positioned. Advantages of this device are the cost, stability, and availability with which hydrodynamic focusing can be achieved; the limitation is the size of the channel and the angle at which the sheath flow meets the analyte flow, which accelerates the transit of particles. These features of the chamber may be altered to ensure the greatest particle detection; an exemplary chamber allowing greater focusing of the analyte flow is shown in FIG. 3B. This chamber model uses a shallow channel 35 for the analyte having a width of the order of 10-20 μm and a depth of 50 μm. A deeper channel 36A and 36B, which intersects with the analyte channel at 90°, is used for the sheath flow, to achieve a greater degree of three-dimensional hydrodynamic focusing, adjusting the relative position of the confocal volume to a region of the focused analyte flow having appropriate acceleration. If particle speed in the analyte flow exceeds the ability of the detector to distinguish individual particles, fewer particles will be detected per unit time. The confocal volume of the laser beam may have a diameter of 0.3 μm and height as low as 1.0 μm, an order of magnitude smaller than the analyte flow, which has dimensions of the order of up to 30-80 μm, as indicted in FIG. 3C. In such a chamber design, optimal hydrodynamic focusing may be reached, such that at least 100 particles can be detected in at most 10 minutes from a solution with particles at a concentration as low as $10^4$ particles/mL. For analysis of specific types of samples and different particles to be detected, alterations in the dimensions, depths, and arrangement of the various channels may be employed to optimize the focusing of the stream of analyte particles. It is to be understood that the microfluidic chambers shown in FIGS. 3A and 3B are exemplary implementations and the disclosed methods and systems are not limited to these designs. The specific design of the chamber should take into account the inverse relationship between the ratio of rates of sheath and analyte flow and cross-sectional area of the analyte flow in the focused area, to find the optimal balance between particle flow speed and particle stream cross-section area relative to the dimensions of the confocal spot. Slower analyte and sheath flows would allow more detection events; however, the lower ratio of the sheath and analyte flows are, the greater will be the cross-section area of the analyte stream, which reduces the number of particles flowing through the confocal volume. These concepts are further illustrated in FIG. 3C. For example, some implementations may use laminar flow without hydrodynamic focusing, through a microfluidics channel whose surface is coated with viral-specific proteins, antibodies, or nanobodies that bind transiently to viral particles as they pass through the channel. Such temporary binding would attenuate the flow and increase the width of the burst, indicating identification of a viral particle.

In FIG. 3C is shown typical fluorescence confocal scanning images of cross-section areas of the hydrodynamically-focused analyte stream in the hydrodynamically-focused region, with 300 nL/min flow rate of fluorescein analyte in the central region of the image and peripheral rhodamine-800 sheath flow at different flow rates of 100 μL/min (left), 250 μL/min (middle) and 700 μL/min (right), using a chamber such as that shown in FIG. 3A. The higher the sheath flow rate relative to the analyte flow rate, the more focused the analyte stream becomes, leading to the detection of more analyte particles passing through the confocal volume. A higher sheath flow rate also causes more predictable and uniform particle detection, and causes less mixing between analyte flow and sheath flow. The system is capable of focusing the analyte stream to a cross section width of 30 μm in one dimension at flow rates of 700 μL/min. Due to the narrowing of the stream of particles via the hydrodynamic focusing effect, focusing in this manner allows to decrease the cross-sectional area of the flowing particles by 3-4 orders of magnitude relative to the initial width of the channel. This adaption allows the characterization of virus particles from bodily fluids at viral loads of $10^4$ particles/mL. Introducing a similar method of analyte focusing also in the height dimension of the channel, using microfluidic designs such as the one shown in FIG. 3B, facilitates the characterization of virus particles at low viral loads of $10^3$ particles/mL or lower, thereby minimizing the number of false negatives in identifying symptomatic patients. These viral loads would be in the physiological range, if the lowest viral load in the saliva of individuals symptomatic for viral infection is $10^3$ particles/mL, as has been found, for example, in saliva samples of COVID-19 subjects within 14 days after appearance of symptoms. The method counts a statistically-sufficient number of detection events (more than 100) in a short period (less than 10 minutes) using flow through a single microfluidic channel with a uniform cross-section area of $100 \times 100 \ \mu m^2$ to $100 \times 1000 \ \mu m^2$. Using microfluidic devices of area $100 \times 1000 \ \mu m^2$, the required sensitivity limit can be reached with a sample containing $10^8$ particles/mL. Reduced cross-sectional dimensionality in the microfluidic flow is especially helpful when high local concentrations are required, especially when the total virus particle concentration is negligible. In contrast to previous methods, an advantage of the present system is the enhanced accuracy in particle size calibration, achieved by the application of iFCS-type detection to the identification of viral particles as void volumes inside a dye solution having precisely known dimensions under laminar flow conditions, without the variance introduced by the randomicity of freely diffusing particles. The disclosed system can detect an average minimal viral load in a given bodily fluid for a pathological condition typically caused by infection with a particular virus. The bodily fluids may comprise any of sputum, serum, cerebral spinal fluid, urine, or feces.

The system's sensitivity allows detection of more than 100 particles in under 10 minutes for a sample with particle concentrations as low as $10^8$ particles/mL using the $100 \times 1,000 \ \mu m^2$ microfluidic channel cutoff. With the $100 \times 100 \ \mu m^2$ microfluidic channel cutoff, a sensitivity of $10^7$ particles/mL can be reached. In general samples of biologically relevant sensitivities from bodily fluids are on the order of $10^7$ particles/mL or less. Using a microfluidic device that concentrates the particles by orders of magnitude enables a similar increase in sensitivity. Therefore, if three-dimensional hydrodynamic flow reduces flow in a $100 \times 1,000 \ \mu m^2$ microfluidic channel to the $2 \times 2 \ \mu m^2$ cutoff, more than 100 particles can be detected in less than 10 minutes for a sample with particle concentrations as low as $4 \times 10^3$ particles/mL.

Figure 4:
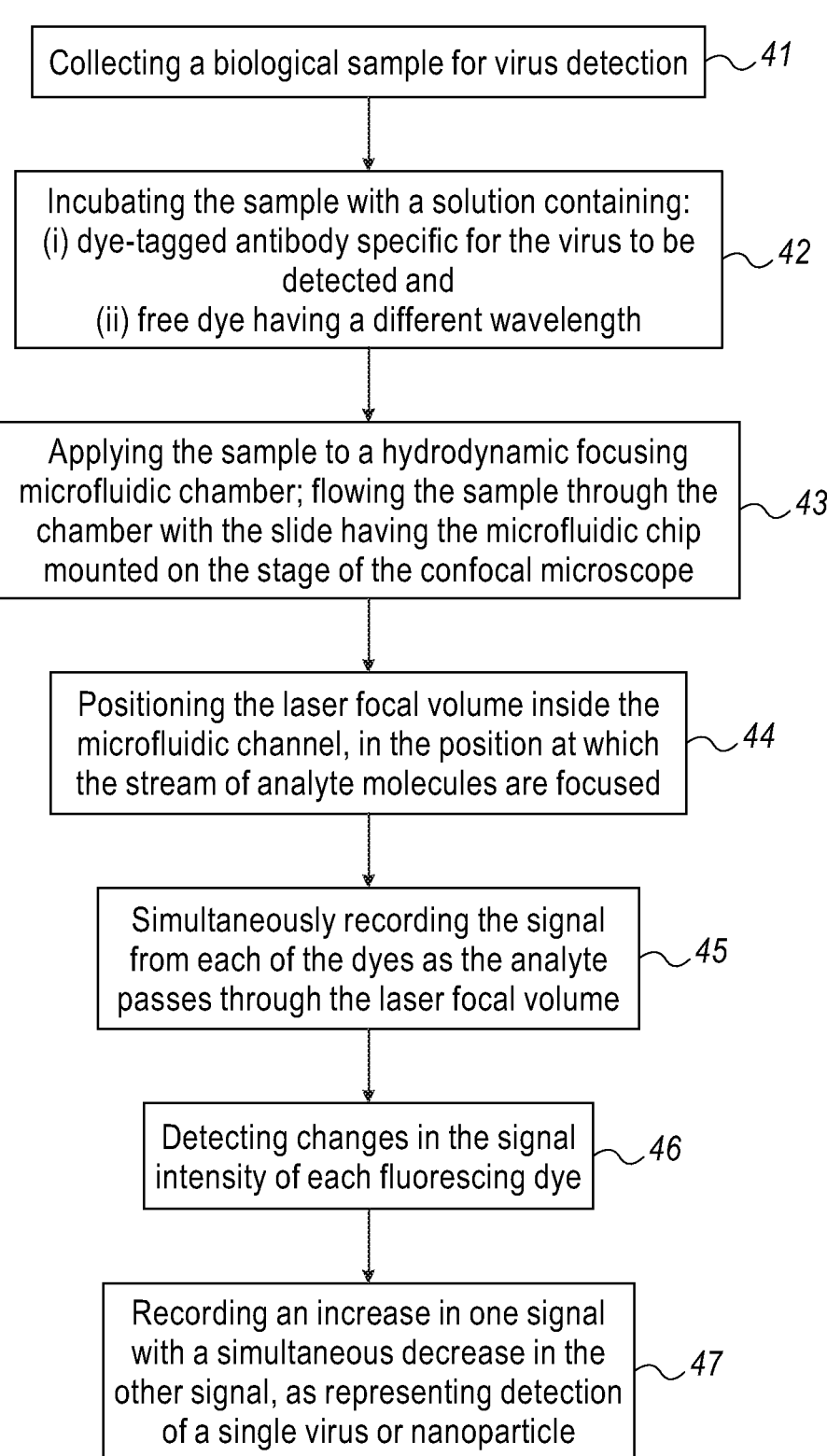
FIG. 4 is a flowchart detailing an exemplary method employing elements of the disclosure.

Reference is now made to FIG. 4, delineating a representative implementation of an exemplary method of the disclosure. In step 41, a biological sample is collected for virus detection. In step 42, the sample is incubated with a solution including a dye-tagged antibody specific for the virus to be detected, and a free dye having a different fluorescence wavelength from the dye bound to the antibody. In step 43, the sample is loaded into a microfluidic chamber adapted for laminar flow and/or hydrodynamic focusing. The sample analyte as well as the buffer sheath flow using syringe pumps, and the slide containing the microfluidic chip is mounted on top of the confocal microscope stage. In step 44, the laser focal volume is positioned inside the microfluidic channel in the position at which the analyte stream is focused, i.e., within the junction of analyte and sheath flows, such that the laser stimulates the excitation wavelengths and detects the emission wavelength, of each dye. In step 45, the detectors simultaneously record the fluorescence signal levels from each of the dyes as the sample passes through the laser focal volume. In step 46, changes in the intensity of each dye signal are detected and recorded over time. In step 47, an increase in one signal combined with a simultaneous decrease in the other signal is recorded as detection of a single virus or other nanoparticle.

Figure 5:
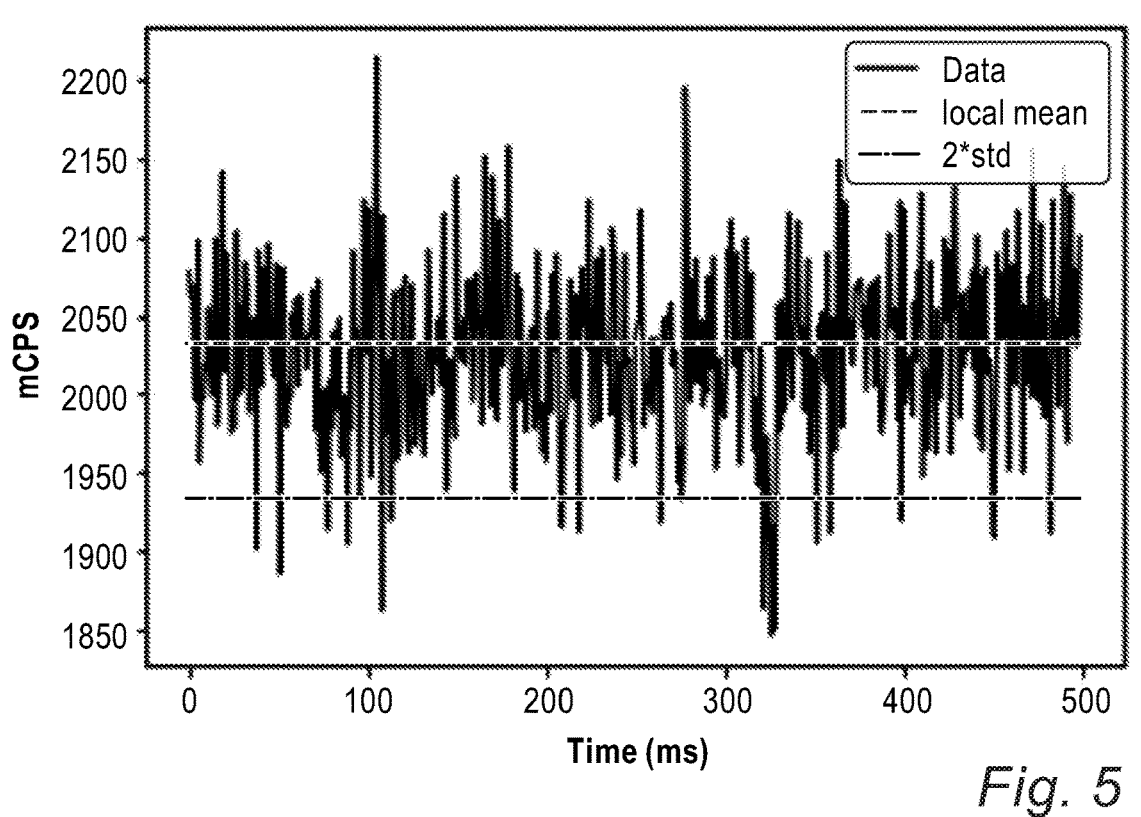
FIG. 5 shows an enlarged plot of a measured fluorescence signal as a function of time, showing the extent of the background noise.
Figure 6:
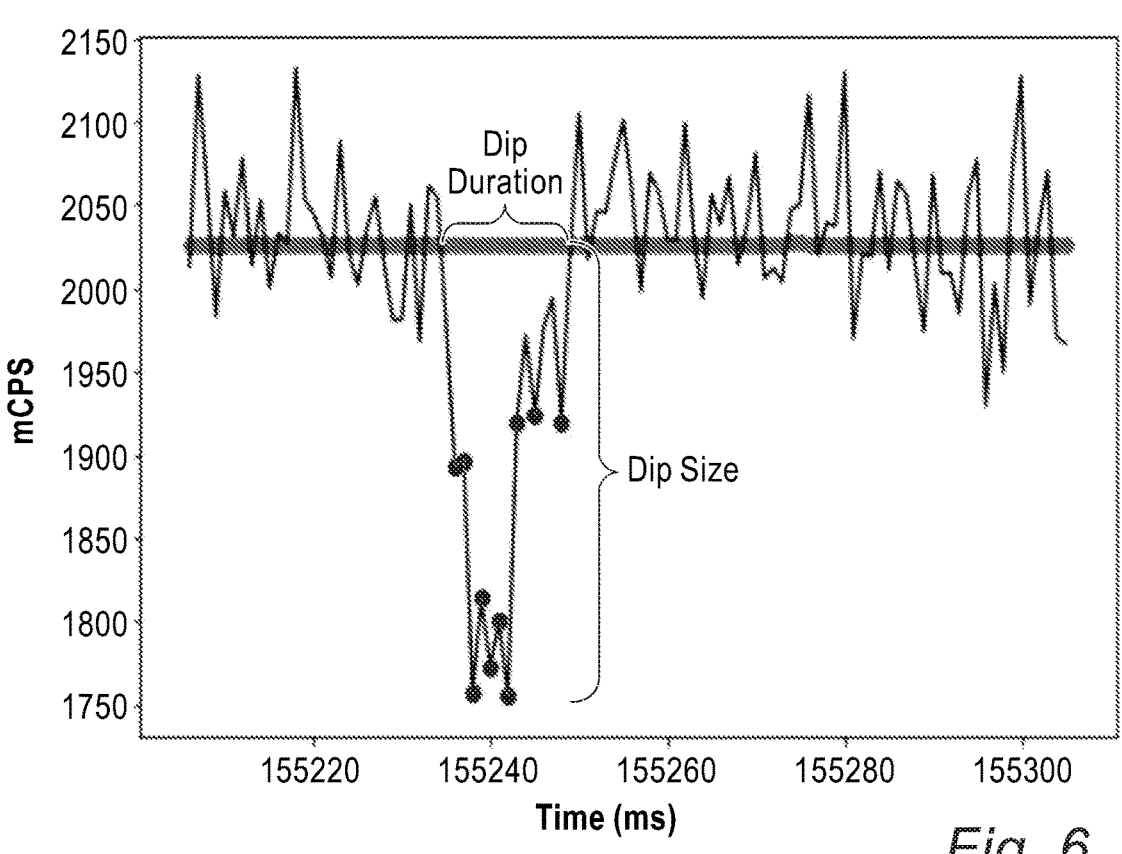
FIG. 6 is an enlarged view of part of a time plot of the fluorescence signal around the occurrence of a dip, showing how the level and duration of the dips and bursts may be defined.
Figure 7:
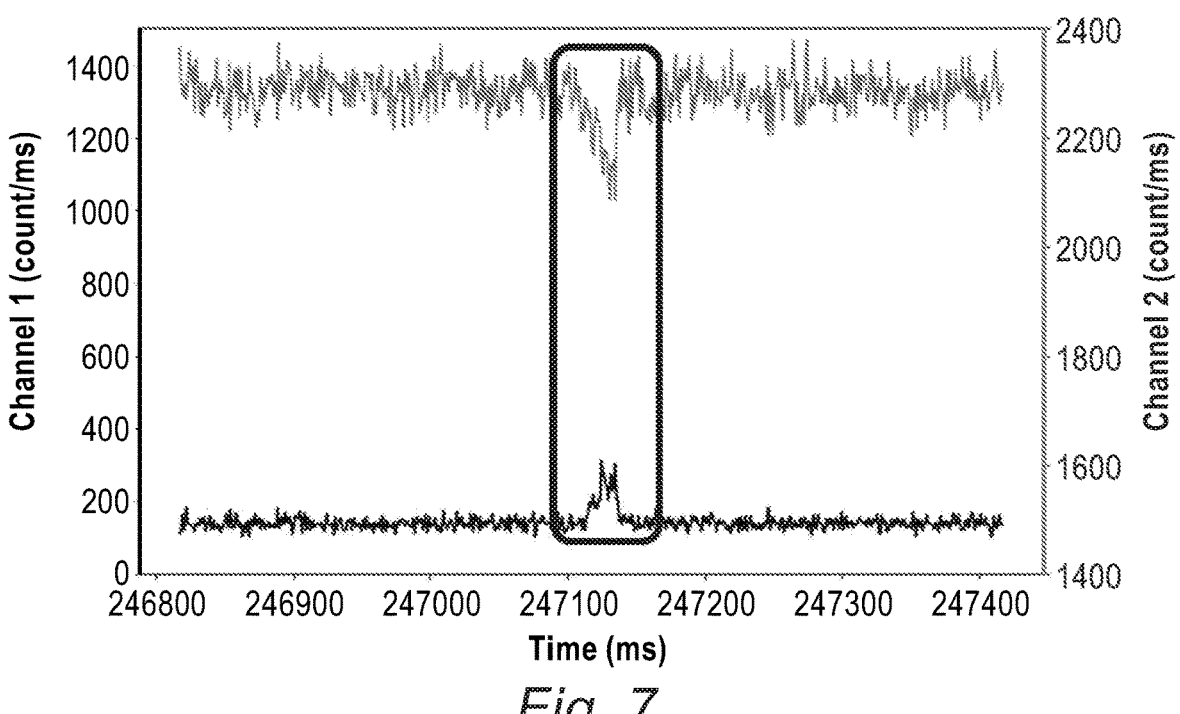

Reference is now made to FIGS. 5 to 7, which illustrate one exemplary way in which the dips and bursts can be identified, and how their sizes and durations can be quantified. As previously explained, when measuring flowing particles in the presence of a high concentration of free dyes, the laser excites the dyes and produces a constant fluorescent signal. When a particle flows through the laser focus, it reduces the overall number of dyes in the region of the laser focus by an amount proportional to the particle volume, which leads to a temporary dip in the constant fluorescent signal. The larger the particle volume is, the larger the dip will be.

The measurement data may be obtained as a text file that contains the value of counts per ms (mCPS) in bins of 1 ms. Typically, a Python Notebook can be used to calculate the size i.e. signal decrease, and duration i.e. the time from the beginning of the signal decrease till its end, of a cross correlation dip-burst. Two detractors may be used, one channel for the dip signal and other channel for the burst signal:

Referring now to FIG. 5, which shows an enlarged plot of a measured fluorescence signal as a function of time, showing the extent of the noise around the average signal. For each data point of each channel, the local median and two standard deviations (2*std) values are calculated (the median and std of the signal of 1 s before and 1 s after the data point). FIG. 5 shows the local median value and the cutoff of points that are lower than the local median by 2 stds.

Reference is now made to FIG. 6, which is an enlarged view of part of a time plot of the fluorescence signal around the occurrence of a dip, showing how the level and duration of the dips and bursts may be defined.

For the Dip channel, data points that are lower than 2 stds from the local median, marked as points on the plot of FIG. 6, and are consecutive, defined as having at least 3 data points with 10 ms interval between them, are considered as a dip. For the Burst channel, data points that are higher than 4 std from the local median and are consecutive, defined as having at list 3 data points with 10 ms interval between them, are considered as a burst.

Reference is now made to FIG. 7 which illustrates how filtering the dips that are cross-correlated with bursts is performed. By recording the events that have a dip and burst at the same time, the signal dip will be synchronized with a burst of photons detected in the other detector. The burst timing can help enhance the identification of the start and stop of the signal dip and the identification of a specific particle.

Figure 8:
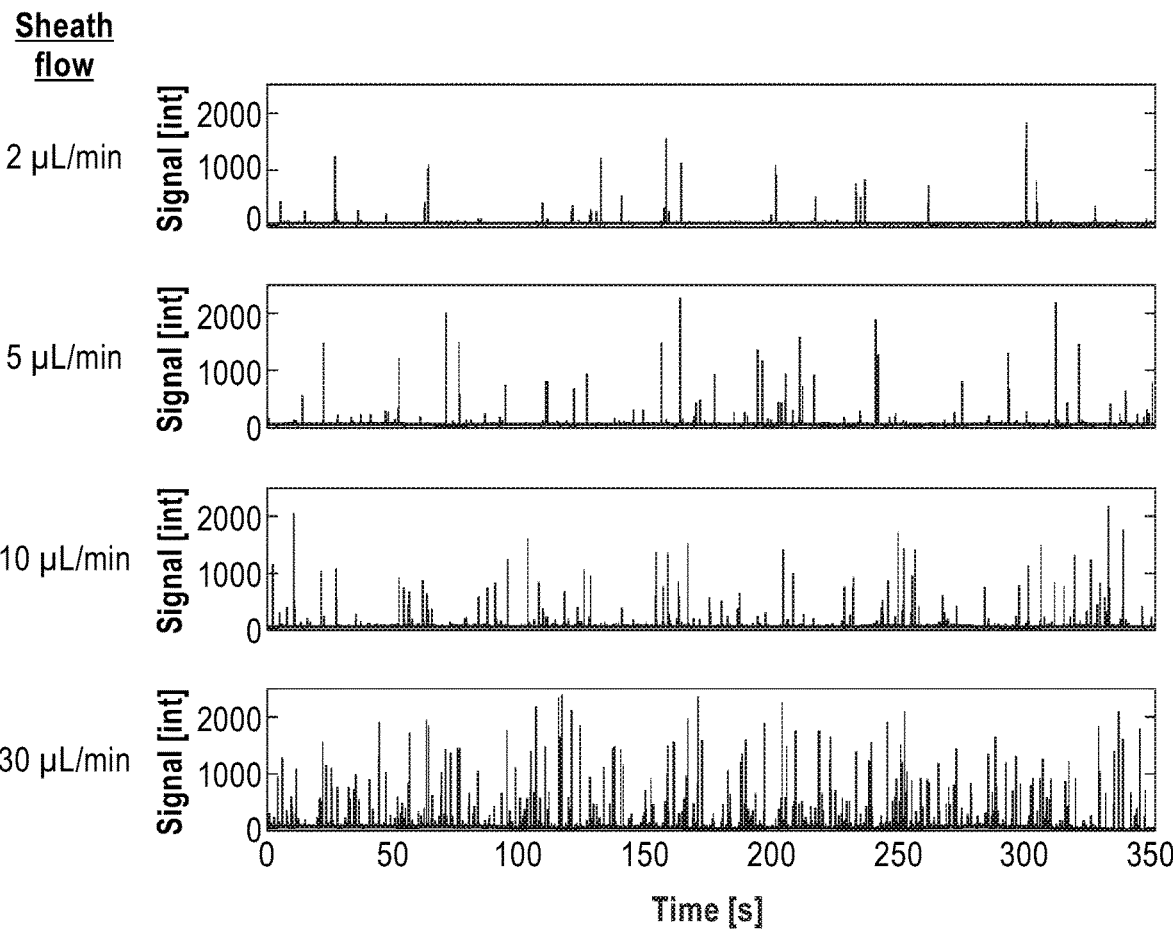
FIG. 8 shows how the detection sensitivity is improved by using improved hydrodynamic focusing.

Reference is now made to FIG. 8, which shows how the detection sensitivity is improved by using improved hydrodynamic focusing. Previously, work by the present applicants, has shown that the detection sensitivity limit, defined as the minimal number of particles per 1 mL that will yield at least 100 detections in at most 10 minutes, is reached on a $10^8$ particles/mL solution, for flowing particles in a microfluidic channel with a $1,000 \times 100 \ \mu m^2$ cross-section. Using a commercial (Ibidi) microfluidic chip, hydrodynamic focusing of an analyte beam width was achieved, from $1,000 \ \mu m$ to $30 \ \mu m$, as shown in FIGS. 3B and 3C hereinabove, thus showing, theoretically, the ability to reach the sensitivity limit at $10^5$ particles/mL solution. This has now been demonstrated on actual bead solutions of $10^4$ particles/mL, thus increasing the sensitivity of detections from approximately 1 detection/min to approximately 30 detections/min, by increasing the sheath flow rate from $2 \ \mu L/min$ to $30 \ \mu L/min$ and keeping the analyte flow rate steady at $1 \ \mu L/min$. The results of such measurements are shown in FIG. 8, where the increase in the number of events recorded increases with increase of the sheath rate of flow. This illustrates the achievement of the required standard of at least 100 detections in less of 10 minutes.

The flow virometer concept is not limited to the exemplary implementations discussed hereinabove. Various nanoparticles serve as models for analysis of more complex and biologically relevant samples, for example, cell exosomes. The setup may be calibrated using beads of different sizes labeled with various wavelength-emitting dyes, mimicking particles of well-known sizes, with large number of dyes bound to their surface. Beads with specific surface interactions are simulated by high-affinity biotin-avidin binding of biotinylated dyes to avidin coating the surface of the beads to mimic high-affinity biological interactions. More complex binding interactions are mimicked by a BSL-2 level virus such as the vesicular stomatitis virus (VSV), having a non-spherical, bullet shape (70 nm width×170 nm length), and targeting a surface G-protein receptor with one of many available dye-labeled antibodies. Further implementations of the setup may be used to detect and quantify the viral load of other viruses such as infective bronchitis viruses (IBV), lentivirus-based SARS-CoV-2 pseudoviruses, and several of the human coronaviruses that cause the common cold other than SARS-CoV-2, in human saliva samples, sputum samples, nose and throat swabs, and other relevant biological samples.

Using calibration of the flow virometer for microchips with 100×1000 μm² and 100×100 μm² uniform cross-sectional areas, spherical particles with diameters as low as 50 nm have been detected with ±50 nm accuracy. The minimal concentration of spherical particles with 100 nm diameter detected within 10 minutes was attainable at a sensitivity limit of $10^7$ particles/mL for a 100×100 μm² uniform cross-sectional microfluidic chip. It was also possible to distinguish 100 nm antibody-labeled particles from 500 nm unlabeled irrelevant particles found in a specimen-like mixture, as shown in FIGS. 2F and 2G. Two-dimensional hydrodynamic focusing allowed reduction in analyte cross-sectional volume, which enabled the sensitivity limit of $10^5$ particles/mL. Using 3D hydrodynamic focusing on a microfluidic chip that facilitates focusing in both dimensions, it may be possible to reach an analyte cross-sectional volume of 2×2 μm², which allows reaching the sensitivity limit with a concentration of $10^3$ particles/mL.

The example of antibody binding to a specific receptor on a virus has been used as a typical implementation of the disclosed methods describing interactions between two members of a pair forming molecular group, wherein "a member of a pair forming molecular group" is a biological molecule capable of binding with specific affinity to another member of the group. The member may comprise one of the pairs: antibody (or antigen binding fragment of antibody) and antigen; lectin and glycoprotein; receptor and ligand; enzyme and substrate; nucleic acid sequence (RNA or DNA), and complementary sequence (RNA or DNA); nucleic acid sequence and aptamer (DNA binding protein). In the case that one member of the pair forming group may comprise an antibody, the antibody may comprise any of: non-human antibody, humanized antibody, human antibody, chimeric antibody, bispecific antibody and an antibody fragment comprising at least the antigen-binding fragment of an antibody. The term "antigen-binding fragment of antibody" may refer to any of: antibody fragment selected from the group consisting of: Fab, Fab', F(ab')2, Fd, Fd', Fv, dAb, isolated CDR region, single chain variable region (scFV), single chain antibody (scab), "diabodies", and "linear antibodies". By non-limiting example, the antibody may be: mouse IgG2a, mouse IgG2b, mouse IgG3, human IgG1, human IgG2, human IgG3, and human IgG4.

Advantages of implementations of the present disclosure over current technology comprise the use of constant, unidirectional flow of the biological sample. Without microfluidic flow, the specific detection of a particular virus in a heterogeneous mixture of particles such as a biological sample, has not been possible. Furthermore, microfluidic flow allows to distinguish particles based on size, which is especially relevant for particles of similar sizes. It is expected that implementations of the above methods may reach a sensitivity of +/−20 nm resolution for size determination of particles. Measuring freely-diffusing particles produces many different detected signal sizes; thus, even if the particles are of the same size, such measurements are irrelevant for correlating the detected signal size to the particle size. Previously, the smallest particle diameter detected was 100 nm. Exemplary methods of the present disclosure allow attainment of a sensitivity of 100 nm diameter particles, allowing detection of a wider range of particles such as viruses, and enabling more sensitive detection of particles at concentrations as low as tens of attomolars (16 aM; $10^4$ particles/mL). Thus, implementations of the present disclosure provide distinct advantages in the specificity and sensitivity of particle detection.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

We claim:

1. A method for detection of a specific nanoparticle in a biological sample, comprising:

a) providing an analyte comprising:

(i) at least a portion of the biological sample, (ii) a first dye having a first fluorescence wavelength, the first dye being able to link to a first member of a pair-forming molecular group, the first member having specific affinity for a second member of the pair-forming molecular group, the second member being attachable to the specific nanoparticle, and (iii) a second dye having a second fluorescence wavelength;

b) narrowing a flow containing the analyte by passing it through a microfluidic device adapted to hydrodynamically focus the flow through a microfluidic channel to concentrate a stream of nanoparticles, the microfluidic channel being positioned in the focal volume of a laser capable of exciting the first dye wavelength and the second dye wavelength; and c) detecting changes in the intensities of a first signal corresponding to the level of fluorescent emission from the first dye and a second signal corresponding to the level of fluorescence emission from the second dye which is free in solution, the emissions resulting from excitation of the dyes by the laser, wherein a decrease in the level of the second signal with a simultaneous increase in the level of the first signal, indicates passage of a single, specific nanoparticle.

2. The method according to claim 1, wherein the specific nanoparticle is any one of a virus, a virus-antibody complex, an exosome, or another nanoparticle having a diameter greater than 100 nm.

3. The method according to claim 1, wherein the biological sample comprises any of sputum, serum, cerebral spinal fluid, urine, or feces.

4. The method according to claim 1, wherein the extent of the decrease in the level of the second signal occurring with a simultaneous increase in the level of the first signal, provides an indication of the volume of a specific nanoparticle.

5. The method according to claim 1, wherein a duration of the increase in the first signal occurring with a simultaneous duration of the decrease in the level of the second signal, provides an indication of the volume of the detected specific nanoparticle.

6. The method according to claim 1, further comprising the use of hydrodynamic focusing inside the microfluidic device to accomplish the narrowing of the analyte flow in the microfluidic channel, for concentrating the flow by a factor of at least 10,000 relative to unconstrained laminar flow in a constant cross-section microfluidic device.

7. The method according to claim 1, wherein the microfluidic channel is mounted on a slide of a confocal microscope.

8. The method according to claim 1, further comprising a step of counting over a predetermined time duration, a number of events showing a decrease in the level of the second signal occurring with a simultaneous increase in the level of the first signal, to provide a quantization of the specific nanoparticles.

9. The method according to claim 1, wherein the specific nanoparticle to be detected is determined by selection of the first dye, according to its ability to link to a first member of the pair-forming molecular group.

10. The method according to claim 1, wherein the first member of the pair-forming molecular group is an antibody, and the second member of the pair-forming molecular group is an antigen.

11. The method according to claim 10, wherein the antigen is a surface molecule on the nanoparticle to be detected, and the nanoparticle is a virus.

12. The method according to claim 10, wherein the antibody comprises any of: a non-human antibody, a humanized antibody, a human antibody, a chimeric antibody, a bispecific antibody, and an antibody fragment comprising at least the antigen-binding fragment of an antibody.

13. The method according to claim 12, wherein the antigen-binding fragment of an antibody may refer to any of: antibody fragment selected from the group consisting of: Fab, Fab', F(ab')2, Fd, Fd', Fv, dAb, isolated CDR region, single chain variable region (scFV), single chain antibody (scab), "diabodies", and "linear antibodies".

14. The method according to claim 1, wherein either:
(i) the first member of the pair-forming molecular group is a lectin, and the second member of the pair-forming molecular group is a glycoprotein, or
(ii) the first member of the pair-forming molecular group is a receptor, and the second member of the pair-forming molecular group is a ligand that binds specifically to the receptor, or
(iii) the first member of the pair-forming molecular group is an enzyme, and the second member of the pair-forming molecular group is a substrate whose reaction is catalyzed by the enzyme, or
(iv) the first member of the pair-forming molecular group is an RNA or DNA nucleic acid sequence, and the second member of the pair-forming molecular group is either a complementary RNA or DNA sequence, or a DNA binding protein aptamer.

15. The method according to claim 1, wherein the first dye is a fluorophore having specific excitation and emission wavelengths, and the second dye is a fluorophore having specific excitation and emission wavelengths that differ from those of the first fluorophore.

16. The method according to claim 1, wherein the changes can be detected with less than 20 μL of the biological sample.

17. The method according to claim 1, wherein the method is capable of detecting at least 100 particles in 10 minutes at concentrations as low as $1 \times 10^4$ particles/mL.

18. The method according to claim 1, wherein generating the hydrodynamic focused laminar flow is accomplished by mixing the analyte flow with two flanking sheath flows joining the analyte flow at a predefined angle.

19. A system for detection of a specific nanoparticle in a biological sample, comprising:
a confocal optical system having a laser illumination source;
a microfluidic device positioned in the focal volume of the confocal optical system, and adapted to generate a hydrodynamically focused laminar flow of an analyte passed therethrough, the analyte comprising at least a portion of the biological sample comprising a first dye emitting a first fluorescence wavelength on excitation by the laser illumination source, and a second dye, which is free in solution, and emitting a second fluorescence wavelength on excitation by the laser illumination source; and
a correlation optical arrangement for outputting as a function of time, a first signal arising from the first fluorescence emission of the first dye, and a second signal arising from the second fluorescence emission of the second dye,
wherein the first dye is selected to bind to a first member of a pair-forming molecular group, the first member having specific affinity for a second member of the pair-forming molecular group, and the second member being attachable to the specific nanoparticle, such that detection by the correlation of a simultaneous decrease in the level of the second signal with an increase in the level of the first signal, indicates passage of a single specific nanoparticle, and
wherein the confocal optical system comprises a dichroic mirror adapted to transmit light emitted from the flow through the microfluidic device having the wavelength of one of the fluorescent emissions, and to reflect light emitted from the flow through the microfluidic device having the wavelength of the other of the fluorescent emissions.

20. The system according to claim 19, wherein the specific nanoparticle is any one of a virus, a virus-antibody complex, an exosome, or another nanoparticle having a diameter greater than 100 nm.

21. The system according to claim 19, wherein the biological sample comprises any of sputum, serum, cerebral spinal fluid, urine, or other bodily fluids.

22. The system according to claim 19, wherein the extent of the decrease in the level of the second signal occurring with a simultaneous increase in the level of the first signal, and the duration of the decrease of the second signal occurring with a simultaneous increase in the level of the first signal, provides an indication of the volume of the detected specific nanoparticle.

23. The system according to claim 19, further comprising the use of hydrodynamic focusing inside a channel of the microfluidic device, the channel being mounted on a microscope glass slide to accomplish the narrowed laminar flow in the microfluidic device, wherein generating the microfluidic hydrodynamic focusing is accomplished by mixing the analyte flow with two flanking sheath flows joining the analyte flow at a predefined angle.

24. The system according to claim 19, further comprising a step of counting over a predetermined time duration, a number of events showing a decrease in the level of the second signal occurring with a simultaneous increase in the level of the first signal, to provide a quantization of the specific nanoparticles.

25. The system according to claim 19, wherein the specific nanoparticle to be detected is determined by selection of the first dye, according to its ability to link to the first member of the pair-forming molecular group, wherein the first member of the pair-forming molecular group is an antibody, and the second member of the pair-forming molecular group is an antigen.

\* \* \* \* \*